Nov. 1, 1949. W. E. SILVA Plant Pat. 890
STRAWBERRY PLANT
Filed Aug. 14, 1948
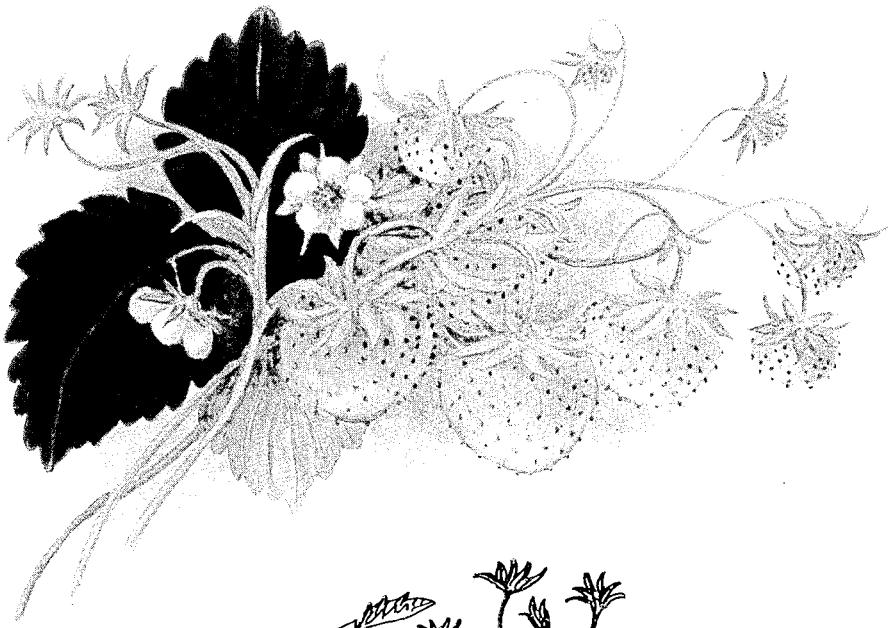
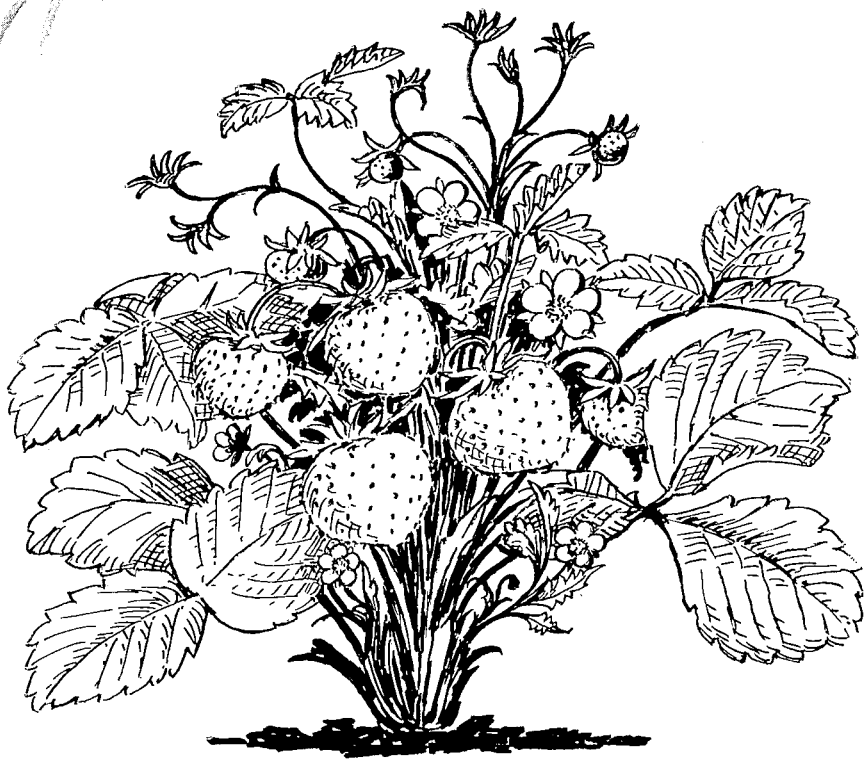
WITNESS
Addison E. Avery
INVENTOR
WILLIAM E. SILVA,
Rummler, Rummler & Snow,
ATTYS.

Patented Nov. 1, 1949

Plant Pat. 890

UNITED STATES PATENT OFFICE

890

STRAWBERRY PLANT

William E. Silva, Sebastopol, Calif.

Application August 14, 1948, Serial No. 44,367

1 Claim. (Cl. 47—62)

This invention relates to a new variety of strawberry plant which has resulted from definite breeding efforts carried on by me since 1945 at my experimental ground at Sebastopol, California, with a view to obtaining improvements as regards quality of fruit and increased everbearing productivity.

My new variety originated as a seedling resulting from pollenation of a parent plant of "Rockhill" variety crossed with pollen taken from a white seeded seedling offspring of "Gem" and "Wyzatia" varieties and which I have propagated asexually by dividing crowns into segments, each comprising a crown portion with roots and leaves.

In our experimental ground it proves to be better than any other variety we have ever grown. It has no runners and produces fruit on all new shoots or stolons. If given water and fertilizer, it produces fruit abundantly all summer and until frost stops growth. It has not yet been tried in parts where there is no frost.

In the drawing, the top view shows in color, the characteristic arrangement of the leaves, berries and flowers on the stems. The lower view shows the typical form and proportions of a field-grown plant of the new variety.

Detailed description of this variety follows:

Seed parent: Rockhill.

Pollen parent: White-seeded seedling obtained by crossing of Gem and Wyzatia varieties.

Plant growth is hardy and upright, 8 inches to 10 inches in height.

Foliage is heavy and large; upper surface dark green, under surface lighter green.

Stems are tall, sturdy, upright, and green in color.

Blooms: Blossoms appear from spring to fall.

*Flower buds.*—Hardy and small.

*Calyx.*—Green and small.

*Petals.*—4 to 6 small and white.

*Anthers.*—Yellow, strong, and heavy.

*Pollen.*—Yellow.

*Filamenta.*—Oblong.

*Pistils.*—Short and greenish white.

Berries: Large, red, sweet, fragrant, heart-shaped, and borne continuously and in heavy production from spring to fall. Flesh color is red and texture firm.

Seeds: Small, conical, and light colored.

The color of the plant is indicated by Maerz & Paul's Dictionary of Color as follows:

| | Plate | Letter | No. |
|---|---|---|---|
| Tip of berry slightly yellow red | 4 | K | 11 |
| Main red of berry | 5 | L | 6 |
| Main leaf green | 23 | L | 9 |
| Blossoms, white. | | | |

The plant has not been described in printed matter or to other persons except for trial as to disease and pest resistance. It is very resistant to various forms of disease.

It does not resemble any known variety and is distinctive as to type and variety. Commencing in the spring, the shoots that are produced in the previous season without runners will throw up new shoots or stolons and each new stolon will bear a flower stem with flowers and fruit, the stem being 5 inches to 8 inches in length with 6 to 10 berries on pedicels 2 inches to 3 inches long. The fruit is of good canning quality.

I claim:

The new and distinct variety of strawberry plant substantially as described and illustrated, characterized by its sturdy growth, productiveness of fruit, and absence of runners.

WILLIAM E. SILVA.

No references cited.